US00PP10778P

United States Patent [19]

Engelke

[11] Patent Number: Plant 10,778

[45] Date of Patent: Feb. 2, 1999

[54] 'CAVALIER' ZOYSIAGRASS PLANT

[75] Inventor: Milton Charles Engelke, Parker, Tex.

[73] Assignee: The Texas A&M University System, College Station, Tex.

[21] Appl. No.: 890,959

[22] Filed: Jul. 8, 1997

[51] Int. Cl.[6] ..... A01H 5/00

[52] U.S. Cl. ..... Plt./90

[58] Field of Search ..... Plt./90

[56] References Cited

U.S. PATENT DOCUMENTS

P.P. 5,845 12/1986 Youngner ..... Plt./90
P.P. 6,529 1/1989 Pursley ..... Plt./90

*Primary Examiner*—Howard J. Locker
*Assistant Examiner*—Kent L. Bell
*Attorney, Agent, or Firm*—Fulbright & Jaworski LLP

[57] ABSTRACT

An asexually reproduced variety of perennial zoysiagrass with a unique combination of characters including an absence of leaf blade hairs, high turf quality, resistance to fall armyworm and a distinct DNA fingerprint.

2 Drawing Sheets

BRIEF SUMMARY OF THE INVENTION

The present invention relates to a new and distinct asexually reproduced variety of perennial zoysiagrass (*Zoysia matrella* (L.)) Merr.

BACKGROUND OF THE INVENTION

This invention relates to a new and distinct perennial zoysiagrass cultivar identified as 'Cavalier' zoysiagrass (hereinafter referred to as 'Cavalier'), that was tested as DALZ8507. 'Cavalier' was discovered in a cultivated area that received mowing and traffic on Seoul National University campus, Suwon, South Korea. It was identified as a unique turfgrass clone growing among a diverse population of common zoysiagrasses native to the area.

For purposes of registration under the "International Convention for the Protection of New Varieties of Plants" (generally known by its French acronym as the UPOV Convention) and noting Section 1612 of the Manual of Plant Examining Procedure, it is proposed that the new variety of zoysiagrass of the present invention be named 'Cavalier' Zoysiagrass.

BRIEF DESCRIPTIONS OF THE ILLUSTRATIONS

DETAILED DESCRIPTION OF THE PLANT

Figure 1:
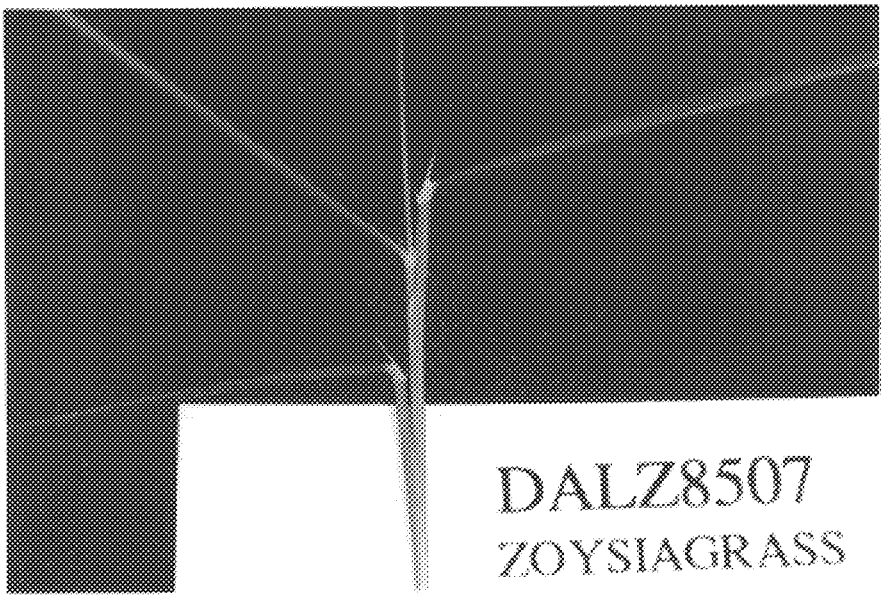
FIG. 1 depicts an up-close view of the leaf blade and ligule of 'Cavalier'.

'Cavalier' was characterized in greenhouse and field conditions. 'Cavalier' is a unique variety of zoysiagrass (*Zoysia matrella* (L.) Merr that was discovered under cultivated conditions described above. 'Cavalier' was asexually reproduced by cutting of stolons and rhizomes, rooting them in soil, and planting of the rooted material to provide planting stock for studying performance and for comparison of morphological characters after propagation. 'Cavalier' has been propagated by sod, plugs, sprigs, and stolons. Seed reproduction with self-fertility is not common in the Zoysia sp. No seedling establishment from 'Cavalier' has been noticed in either greenhouse or field studies.

'Cavalier' spreads primarily by stolons. It has an intermediate to rapid growth rate, and has intermediate to low water use requirements. 'Cavalier' produces little thatch with an optimum mowing height of ⅜" to 2.5". 'Cavalier' will generally cover in 10–12 months growing time when plug planted with 3"×4" plugs planted on 12" centers or by sprigs.

'Cavalier' has both rhizome and stolon growth. The stolons of 'Cavalier' have a mean internode length of 16.7 mm between the fourth to the fifth node, 18.4 mm between the second and third nodes, with a mean stolon width and diameter from 1.35 to 1.14 mm (Tables 1,2). The stolons of 'Cavalier' root adventitiously at the nodes. Color notations of plant tissues were based on the Munsell *Color Charts for Plant Tissues*, Munsell Color, Baltimore, Md., 1977. Light quality, photoperiod, and general growth of the plants affect color notations. The internode stolon color of 'Cavalier' stolons exposed to full sun is 5R 3/6.

Leaf blades of 'Cavalier' are rolled in the bud, and are flat and stiff. The leaf blade length of 'Cavalier' ranges from 58.9 to 60.7 mm and from 1.33 to 1.79 mm in width (Table 3,4,5), shorter and narrower than 'El Toro' and 'Meyer'. There are not any hairs on the abaxial/adaxial leaf surfaces of 'Cavalier'. Measured under greenhouse conditions in January 1996, the genetic, adaxial leaf color of 'Cavalier' is 2.5 GY 5/2 with 'El Toro' having a leaf color of 2.5 GY 5/2, and 'Meyer' having a color of 2.5 G 3/4. The ligule of 'Cavalier' is a row of silky hairs, approximately 2.1mm in length on the longest hairs.

The flat leaf length of 'Cavalier' is a mean of 2.66 cm when measured in a greenhouse, Dallas, Tex., January 1996. 'Cavalier' has 2.5 GY 7/4 anthers and white colored stigmas, undistinguished in shade of color. The inflorescence of 'Cavalier' is a terminal spike-like raceme, with spikelets on short pedicels. 'Cavalier' has a mean culm length of 4.5 cm, a floral region of 13.3 mm, with a mean of 16.3 florets per raceme.

The chromosome number of 'Cavalier' is 40.

'Cavalier' rated number one in the National Turf Evaluation Program (NTEP) trials over 4-yrs as tested at 24 locations ranging from California–Georgia and north to Nebraska and Colorado. 'Cavalier' will find its primary utility in home lawns, golf course fairways and tee boxes and in parks and recreational areas (Table 6).

This test was planted into a sited shaded with live oak trees in 1 Sep,. 1992. Under tree shade with competition from trees for available moisture and nutrients, 'Cavalier' had slightly more cover than 'Belair' and 'Meyer' (Table 7).

When 'Cavalier' was compared with 59 other zoysiagrasses for salinity tolerance, it ranked number 22 in performance that was not different in injury rating for 'Emerald' and superior to 'Belair', and 'Meyer' (Table 8). When compared to other commercial varieties for root growth, 'Cavalier' produced shorter average root depth, less root weight than 'Emerald', and clipping weights similar to 'Emerald' (Table 9).

Nine zoysiagrass cultivars were tested for resistance to the fall armyworm (*Spodoptera frugiperda*) in laboratory tests (Table 10). Eggs of the fall armyworm (FAW) were obtained from the colony maintained at the USDA Laboratory at Tifton, Ga. Larvae were developed from the eggs, and feed with zoysiagrass tissue of the cultivars, with days to pupation and adult emergence of the FAW used as indicators of FAW resistance. When neonate larvae of FAW were confined on the zoysiagrass cultivars, less than 5% of the larvae survived beyond 4 days of 'Cavalier', 'Emerald', or 'Belair'. Two cultivars, 'Palisades' and '8516' were among the most susceptible with 57% and 55% survival respectively to 17 days and longer. No larvae were able to survive to 17 days on the cultivar 'Cavalier', indicating the resistance of 'Cavalier' to FAW was in the form of larval mortality and an extended development period (Table 10).

'Cavalier' is distinguished from other zoysiagrass by its fine texture, long-narrow leaf, with low rhizome, but high stolon production. It has good to excellent salt tolerance, and good shade tolerance. 'Cavalier' is resistant to the fall armyworm and the tropical sod webworm. 'Cavalier' is intermediate in its growth and recovery rate. 'Cavalier' has good to excellent winter hardiness and will persist in regions north to Kansas, Missouri and Southern Illinois.

TABLE 1

Internode length as measured between the second and third nodes, internode diameter of the third internode, and node diameter of the third node measured on zoysiagrass plants. Plants were grown in a growth chamber with a 14-hour daylength, March 1995.

| Genotype | Internode length --mm-- | Internode diameter --mm-- | node diameter --mm-- |
|---|---|---|---|
| 'Cavalier' | 18.4a* | 1.35abc | 1.35abc |
| 'El Toro' | 39.8a | 1.45abc | 1.45abc |
| 'Meyer' | 24.1a | 1.99a | 1.99a |

*Analysis of variance by General Linear Models, with means followed by the same letter not significantly different using Tukey's Studentized Range (HSD), alpha = 0.05. Only selected means presented.

TABLE 2

Zoysiagrass internode lengths and stolen width measurements from the fourth to the fifth nodes taken February 1988 on greenhouse grown plants.

| Genotype | Internode length --mm-- | Stolon width --mm-- |
|---|---|---|
| 'Cavalier' | 16.73bc* | 1.14efg |
| 'Emerald' | 6.21e | 1.02ghi |
| 'Meyer' | 16.47bc | 1.53b |

*Analysis of variance by General Linear Models, with means followed by the same letter not significantly different using Tukey's Studentized Range (HSD), alpha = 0.05. Only selected means presented.

TABLE 3

Zoysiagrass leaf measurements taken February 1988 on the fourth youngest leaf from greenhouse grown plants.

| Genotype | Blade width --mm-- | Blade length --mm-- |
|---|---|---|
| 'Cavalier' | 1.79ij* | 58.87e |
| 'Emerald' | 2.01fgh | 30.56ff |
| 'Meyer' | 33.3b | 82.33d |

*Means followed by the same letter are not significantly different using the Waller-Duncan k ratio test (k ratio = 100). Only selected means presented.

TABLE 4

Leaf blade width and length measured on the third youngest leaf of zoysiagrasses. Plants were growing in a growth chamber with a 14-hour daylength, March 1995.

| Genotype | Blade width --mm-- | Blade length --mm-- |
|---|---|---|
| 'Cavalier' | 1.33d* | 60.7cd |
| 'El Toro' | 3.26abc | 68.3bcd |
| 'Meyer' | 2.59c | 74.3bc |

*Analysis of variance by General Linear Models, with means followed by the same letter not significantly different using Tukey's Studentized Range (HSD), alpha = 0.05. Only selected means presented.

TABLE 5

Zoysiagrass leaf sheath length measurements taken February 1988 on the fourth youngest leaf from greenhouse grown plants.

| Genotype | Sheath length --mm-- |
|---|---|
| 'Cavalier' | 28.90ef* |
| 'Emerald' | 16.31ij |
| 'Meyer' | 30.68ed |

*Means followed by the same letter are not significantly different using the Waller-Duncan k ratio test (k ratio = 100). Only selected means presented.

TABLE 6

Mean turfgrass quality ranges of vegetative zoysiagrass cultivars grown in the National Turfgrass Evaluation Program at 23 locations in the US for 1992, 1993, and 1994.

| Variety | 1992 | 1993 | 1994 | 1995 | Overall 4-Yr Avg. |
|---|---|---|---|---|---|
| 'Cavalier' (DALZ8507) | 5.95 | 6.23 | 5.89 | 5.99 | 5.93 |
| 'Marquis' (TC 2033) | 5.85 | 6.10 | 6.11 | 5.96 | 5.91 |

TABLE 6-continued

Mean turfgrass quality ranges of vegetative zoysiagrass cultivars grown in the National Turfgrass Evaluation Program at 23 locations in the US for 1992, 1993, and 1994.

| Variety | 1992 | 1993 | 1994 | 1995 | Overall 4-Yr Avg. |
|---|---|---|---|---|---|
| 'Sunburst' | 5.83 | 5.91 | 5.81 | 5.87 | 5.85 |
| 'TC 5018' | 5.80 | 5.81 | 5.92 | 5.70 | 5.81 |
| 'Emerald' | 5.74 | 6.21 | 6.05 | 5.73 | 5.79 |
| 'Omni' (CD 2013) | 5.56 | 6.13 | 6.06 | 5.96 | 5.73 |
| 'QT 2004' | 5.63 | 6.01 | 5.86 | 5.57 | 5.63 |
| 'DALZ 8508' | 5.59 | 6.06 | 5.74 | 5.60 | 5.60 |
| 'Palisades' (DALZ8514) | 5.82 | 5.82 | 5.46 | 5.44 | 5.59 |
| 'Royal' (DALZ9006) | 5.65 | 6.05 | 5.59 | 5.54 | 5.59 |
| 'Crowne' (DALZ8512) | 5.80 | 5.76 | 5.50 | 5.45 | 5.55 |
| 'El Toro' | 5.78 | 5.63 | 5.34 | 5.41 | 5.50 |
| 'CD 259-13' | 5.30 | 5.53 | 5.74 | 5.49 | 5.40 |
| 'Meyer' | 5.26 | 5.70 | 5.76 | 5.47 | 5.39 |
| 'QT 2047' | 5.37 | 5.39 | 5.26 | 5.16 | 5.30 |
| 'Belair' | 4.99 | 5.58 | 5.61 | 5.02 | 5.16 |
| 'DALZ 8516' | 4.72 | 5.42 | 4.96 | 5.05 | 4.86 |
| 'Diamond' (DALZ8502) | 4.40 | 5.03 | 4.58 | 4.36 | 4.41 |
| 'DALZ 8501' | 4.88 | 4.31 | 3.99 | 4.05 | 4.27 |
| 'DALZ 8701' | 4.23 | 4.10 | 3.71 | 3.58 | 3.85 |
| LSD VALUE | 0.22 | 0.20 | 0.20 | 0.20 | 0.17 |

To determine statistical differences among entries, subtract one entry's mean from another entry's mean. Statistical difference occurs when this value is larger than the corresponding LSD value (LSD 0.05).

In National Zoysiagrass Test - 1991. Final Report 1992–95, NTEP No. 96-15; (Table 4); United States Department of Agriculture, Agricultural Research Service, Beltsville Agricultural Research Center, Beltsville, MD 20705.

TABLE 7

Mean turf cover, as percentage of plot during turf, during winter 1993–1994 for the 1991 NTEP zoysia trial planted under 80% shade in Dallas, TX.

| | Percentage Turf Cover | | |
|---|---|---|---|
| Variety | 10 Nov 93 | 21 Dec 93 | 22 March 94 |
| 'Belair' | 40.0 | 43.3 | 21.7 |
| 'Cavalier' | 48.3 | 55.0 | 26.7 |
| 'Emerald' | 41.7 | 51.7 | 26.7 |
| 'El Toro' | 35.0 | 31.7 | 21.7 |
| 'Meyer' | 33.3 | 38.3 | 23.3 |
| MSD | ns | 14.5 | 10.2 |

MSD is the minimum significant difference between entry means for comparison within column, and was based on the Duncan Waller k-ratio test (k-ratio = 100). Only selected means presented.

In Morton, S. J., M. C. Engelke, and K. G. Porter. 1994. Performance of three warm-season turfgrass genera cultured in shade III. Zoysia spp. In Texas Turfgrass Research Report - 1994. PR. 5242. p 27–29.

TABLE 8*

Average percent shoot salt injury (average of 20 rating dates) on zoysiagrass entries in the 1991 NTEP† Trials.

| Entry | Source | Species‡ | % Injury |
|---|---|---|---|
| 'Diamond' | NTEP 20 | *matrella* | 33ab |
| 'El Toro' | NTEP 13 | *japonica* | 38a–e |
| 'Emerald' | NTEP 10 | *jap x tenu* | 42a–h |
| 'Cavalier' | NTEP 17 | *matrella* | 42a–h |
| 'Belair' | NTEP 11 | *japonica* | 50f–k |

TABLE 8*-continued

Average percent shoot salt injury (average of 20 rating dates) on zoysiagrass entries in the 1991 NTEP† Trials.

| Entry | Source | Species‡ | % Injury |
|---|---|---|---|
| 'Meyer' | NTEP 09 | *japonica* | 58lmn |
| 'Korean Common' | NTEP 07* | *japonica* | 76pq |

*Selected data set; complete data set includes 59 varieties and cultivars.

†NTEP = National Turfgrass Evaluation Program.

‡Species identity.

£Means followed by the same letter are not significantly different, based on the Waller-Duncan k-ratio t-test (k-ratio = 100)

In Marcum, K. B., M. C. Engelke, S. J. Morton and C. Dayton. 1994. Salinity tolerances of selected bermudagrass and zoysiagrass genotypes. TX Turfgrass Res. - 1993, Consolidated Prog. Rep. PR 5140: 105–107.

TABLE 9

Average mean root depth of zoysiagrasses grown in flexible tubes in greenhouse studies, Dallas, TX.

| Variety | Average Mean Root Depth --mm-- | Total Root Weight --mg-- | Clipping Weight --mg-- |
|---|---|---|---|
| 'Belair' | 296 | 330 | 286 |
| 'Cavalier' | 255 | 278 | 243 |
| 'El Toro' | 356 | 473 | 391 |
| 'Emerald' | 330 | 461 | 241 |
| 'Meyer' | 333 | 411 | 466 |
| MSD | 79 | 161 | 267 |

*MSD = minimum significant difference for comparison of means within columns based on the Waller-Duncan k-ratio test where k = 100. Only selected means presented.

In Marcum, K. B., M. C. Engelke, S. J. Morton, and R. H. White. 1995. Rooting charcteristics and associated drought resistance of zoysiagrasses. Agron. J. 87: 534–538.

TABLE 10

Resistance in zoysiagrass to 4-day old larvae of the fall armyworm; survival, weight, and development time.

| Cultivars | 7 day larva | | Pupa | | | Adult | |
|---|---|---|---|---|---|---|---|
| and Genotypes | alive %[1] | wt mg[2] | alive %[3] | wt mg[4] | days[5] | alive %[6] | days[7] |
| 'Cavalier' | 0 | — | 0 | — | — | 0 | — |
| 'DALZ8501' | 14.8 | 34.9a[8] | 11.1 | 151.2ab | 30.0a | 11.1 | 40.0a |
| 'K.Common' | 14.8 | 41.2ab | 11.1 | 136.1ab | 30.3a | 11.1 | 40.7a |
| 'Belair' | 25.9 | 75.5b | 25.9 | 149.8ab | 27.7ab | 25.9 | 37.6abc |
| 'El Toro' | 33.3 | 58.7ab | 26.7 | 171.1a | 29.0a | 26.7 | 39.0a |
| 'Emerald' | 37.0 | 52.1ab | 37.0 | 137.5ab | 30.5a | 37.0 | 40.5a |
| 'Meyer' | 60.0 | 55.4ab | 53.1 | 148.3ab | 28.9a | 53.3 | 38.8ab |
| 'Palisades' | 66.7 | 131.6c | 66.7 | 122.7b | 25.2b | 66.7 | 35.3bc |
| 'DALZ8516' | 81.5 | 143.9c | 74.1 | 156.7ab | 25.1b | 74.1 | 34.7c |

[1]Number of surviving 17-day-old-larvae.
[2]Mean larval weight taken after 17 days of feeding.
[3]Number surviving to pupation.
[4]Mean weight of pupa within 2 days of pupation.
[5]Mean number of days to pupation.
[6]Mean survival to adult.
[7]Mean number of days from egg hatch to adult emergence.
[8]Means in a column followed by the same letter are not significantly different by Waller-Duncan k-ratio t test (k = 100) (P = 0.05)

In Reinert, J. A., M. C. Engelke, S. J. Morton, P. S. Graff, and B. R. Wiseman. 1994. Resistance in zoysiagrass (Zoysia spp) to the fall army worm (*Spodoptera frugiperda*). TX turfgrass Research-1992. Consolidated Prog. Rep. PR 5248: 39–4

EXAMPLE 1

DNA Fingerprint Analysis

See Caetano-Annollés, B. J. Bassam and Peter M. Gresshoff, 1991, DNA Amplification fingerprinting using very short arbitrary oligonucleotide primers. Biotechnology. Vol. 9. Pp. 553–557.

Figure 2:
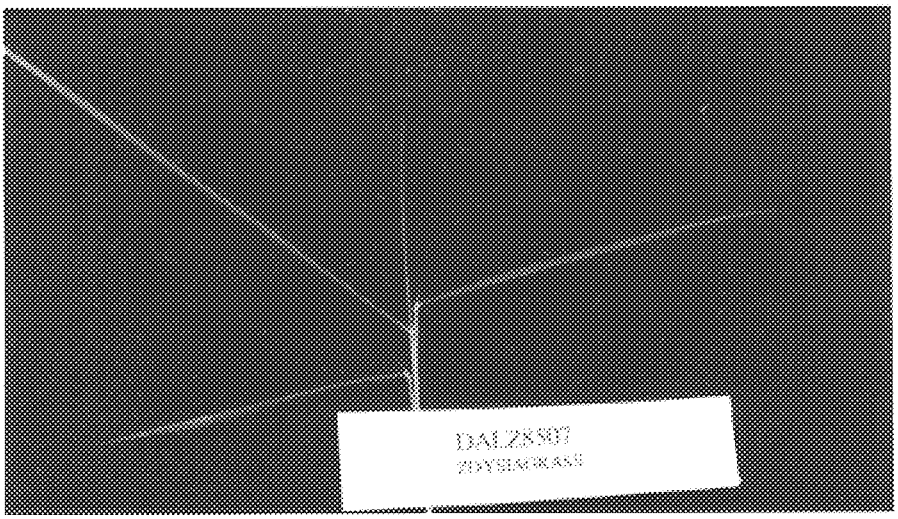
FIG. 2 depicts entire leaf blades and ligule of 'Cavalier'.
Figure 3:
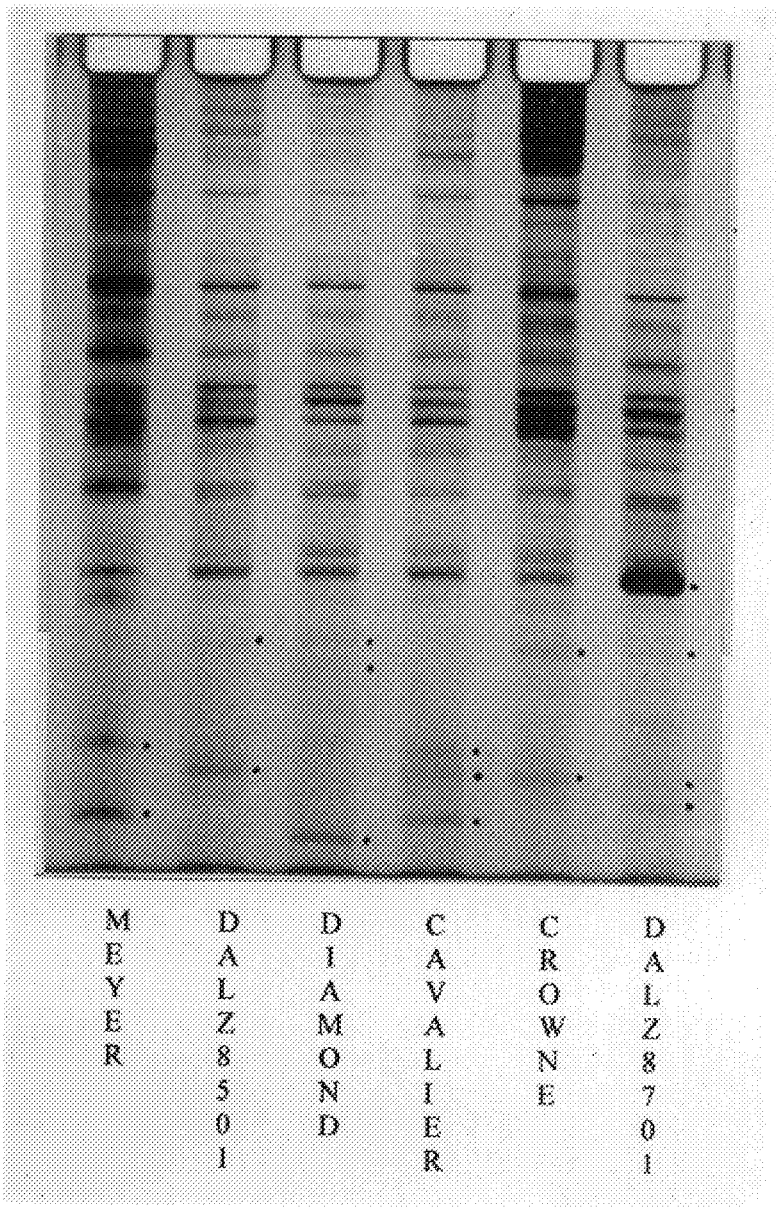
FIG. 3 is a DNA fingerprint of 'Cavalier' in comparison with known varieties of zoysiagrass.

The zoysiagrass amplification profiles were obtained using primer of sequence GCCCGCCC, and are compared to the standard 'Meyer' (FIG. 2). Complex banding patterns and amplification fragment length polymorphisms were obtained in all cases. Results indicate bands fall into two categories, those that are common to the species, and those that in combination are characteristic of the cultivar (some identified by dots).

Statistical Analysis

Statistical analysis performed utilizes the method set forth in Steel and Torrie, 1960, Principles and Procedures of Statistics. Pages 1–481. McGraw-Hill Book Company, Inc. New York.

I claim:

1. A new and distinct variety of zoysiagrass (*Zoysia matrella* (L.) Merr.) plant as described and illustrated herein, having the principle distinguishing characteristics of white stigmas, and absence of leaf blade hairs, high turf quality, resistance to fall armyworm and a distinct DNA fingerprint.

* * * * *

UNITED STATES PATENT AND TRADEMARK OFFICE

CERTIFICATE OF CORRECTION

PATENT NO. : PP10,778
DATED : February 2, 1999
INVENTOR(S) : Milton Charles Engelke It is certified that error appears in the above-identified patent and that said Letters Patent is hereby corrected as shown below:

On page 1,
Lines 13-14, please delete "Seoul National University campus, Suwon, South Korea" and insert -- at the O-nejime, Japan government offices --.

Signed and Sealed this

Third Day of July, 2001

*Attest:*

Nicholas P. Godici

NICHOLAS P. GODICI
*Acting Director of the United States Patent and Trademark Office*

*Attesting Officer*